(12) United States Patent
Joseph et al.

(10) Patent No.: US 11,833,328 B2
(45) Date of Patent: *Dec. 5, 2023

(54) TREATMENT SYSTEM WITH AUTOMATED CANNULA AND SENSOR INSERTER, FLUID DELIVERY DEVICE, AND DRIVE MECHANISM FOR USE THEREWITH

(71) Applicants: Jerry Joseph, Gaithersburg, MD (US); Guilherme de Paula, Sunnyvale, CA (US)

(72) Inventors: Jerry Joseph, Gaithersburg, MD (US); Guilherme de Paula, Sunnyvale, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/999,828

(22) Filed: Aug. 21, 2020

(65) Prior Publication Data
US 2020/0405956 A1 Dec. 31, 2020

Related U.S. Application Data

(63) Continuation of application No. 15/911,094, filed on Mar. 3, 2018, now Pat. No. 10,792,425.
(Continued)

(51) Int. Cl.
| | |
|---|---|
| *A61M 5/172* | (2006.01) |
| *A61M 5/155* | (2006.01) |
| *A61M 5/145* | (2006.01) |
| *A61M 5/158* | (2006.01) |
| *A61M 5/14* | (2006.01) |

(52) U.S. Cl.
CPC ........ *A61M 5/1723* (2013.01); *A61M 5/1407* (2013.01); *A61M 5/14526* (2013.01); *A61M 5/155* (2013.01); *A61M 5/158* (2013.01); *A61M 2005/14506* (2013.01);
(Continued)

(58) Field of Classification Search
CPC .......... A61M 2005/14506; A61M 2005/1585; A61M 2230/06; A61M 2230/201; A61M 5/1407; A61M 5/14526; A61M 5/155; A61M 5/158; A61M 5/1723; A61M 5/168; A61M 5/14; A61M 5/172; A61M 2005/1726; A61M 5/1408; A61M 5/1452; A61M 5/145; A61M 5/142; A61M 5/1422;
(Continued)

(56) References Cited

U.S. PATENT DOCUMENTS

| | | | | |
|---|---|---|---|---|
| 4,381,006 A | * | 4/1983 | Genese | A61M 5/1454 222/340 |
| 5,637,095 A | * | 6/1997 | Nason | A61M 5/14244 604/154 |

(Continued)

*Primary Examiner* — Jason E Flick
(74) *Attorney, Agent, or Firm* — Law Office of Jerry Joseph, PLC; Jerry K. Joseph

(57) ABSTRACT

A treatment system configured to treat a disease using a first therapeutic fluid, the treatment system including a base housing, a first reservoir configured to store a first therapeutic fluid disposed within the base housing, a first plunger disposed within the first reservoir, a first rotatable shaft member configured to rotate within the base housing, and a first flexible member having a first end coupled to the first plunger and a second end coupled to the first rotatable shaft member, wherein the first rotatable shaft member is configured to shorten a length of the first flexible member to deliver the first therapeutic fluid from the first reservoir.

19 Claims, 19 Drawing Sheets

Related U.S. Application Data

(60) Provisional application No. 62/466,408, filed on Mar. 3, 2017.

(52) U.S. Cl.
CPC ............... *A61M 2005/1585* (2013.01); *A61M 2205/368* (2013.01); *A61M 2230/06* (2013.01); *A61M 2230/201* (2013.01)

(58) Field of Classification Search
CPC .... A61M 2005/31518; A61M 5/31511; A61M 5/1456; A61M 5/1454; A61M 2005/14533
See application file for complete search history.

(56) References Cited

U.S. PATENT DOCUMENTS

| | | | | |
|---|---|---|---|---|
| 7,128,727 B2 * | 10/2006 | Flaherty | ................. | G16H 20/17 604/131 |
| 7,713,238 B2 * | 5/2010 | Mernoe | ............. | A61M 5/14566 604/131 |
| 8,585,657 B2 * | 11/2013 | Colton | ................ | A61M 5/1456 604/209 |
| 2007/0073228 A1 * | 3/2007 | Mernoe | ............. | A61M 5/14566 604/131 |
| 2017/0182242 A1 * | 6/2017 | Galitz | .................... | A61M 5/20 |

* cited by examiner

DETAIL A
SCALE 4 : 1

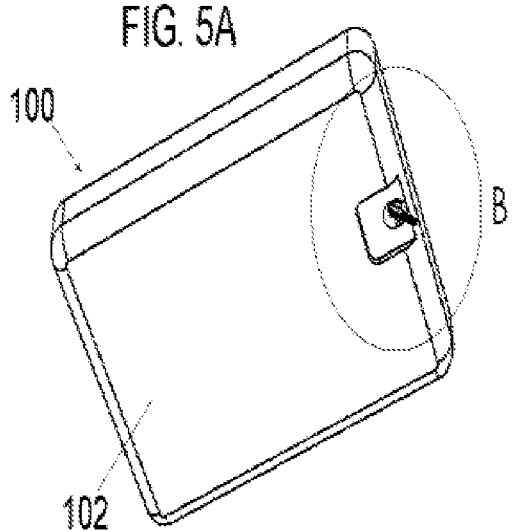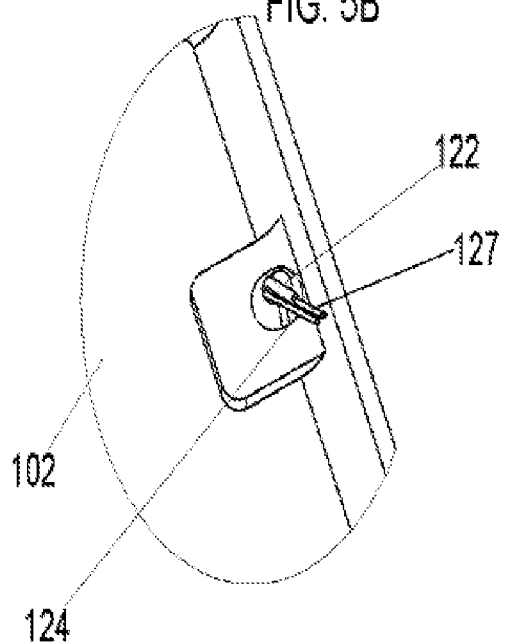

DETAIL C
SCALE 4 : 1

TREATMENT SYSTEM WITH AUTOMATED CANNULA AND SENSOR INSERTER, FLUID DELIVERY DEVICE, AND DRIVE MECHANISM FOR USE THEREWITH

BACKGROUND OF THE INVENTION

1. Field of the Invention

The present general inventive concept relates to a treatment system, and more particularly to devices, systems, and methods capable of monitoring body signals of particular conditions or diseases, including blood glucose levels and treating a user by selectively delivering an appropriate amount of one or more therapeutic agents, fluids, or drugs based on the monitored body signals.

2. Background of the Invention

There currently exists several diseases and conditions which are monitored and/or treated by therapeutic agents and/or medicines. These diseases may be diagnosed and treated based upon the existence or non-existence of particular enzymes, proteins, glucose, and/or other chemicals within a patient's body.

For instance, diabetes is a disease which can be characterized by the absence or improper utilization of insulin secreted by a patient's pancreas. Insulin is used by the body to facilitate the delivery of glucose into cells. Typically, in mammals, the body maintains a blood glucose level at a range between 64.8 and 104.4 mg/dL. Glucose is the main source of energy for body cells and is transported throughout the body through the bloodstream. Glucose requires the hormone insulin in order to be absorbed by the body cells. Many people having various types of diseases and conditions, including diabetes, may need to inject one or more therapeutic agents to more effectively treat and manage their disease or condition.

As such, there is a need for devices, systems, and methods which may treat diseases and conditions by selectively administering one or more therapeutic agents including insulin and glucagon based on data received from one or more integrated sensors.

BRIEF SUMMARY OF THE INVENTION

The present general inventive concept relates to devices, systems, and methods capable of monitoring body signals of particular conditions or diseases, including blood glucose levels and treating by selectively delivering an appropriate amount of one or more therapeutic agents, fluids, or drugs based on the monitored body signals.

The present general inventive concept also relates to a drive system including a propellant enclosed in an expandable membrane which is heated by a heat source (e.g., light or other energy) to push/pull on a system of gears to pull a plunger disposed in a fluid reservoir.

Features and/or utilities of the present general inventive concept may be achieved by providing a treatment system configured to treat a condition using a first fluid, the treatment system including a first reservoir configured to store a first fluid, a cannula insertion mechanism configured to insert a cannula into a user, the cannula in fluid communication with the first reservoir, a first rotatable shaft member configured to pull a first plunger disposed within the first reservoir and coupled to the first rotatable shaft member by a first flexible member, and a drive mechanism having a first expandable member configured to move from a first position to a second position to rotate the first rotatable shaft member to deliver the first fluid to the user through the cannula.

The first fluid may include a first therapeutic agent.

The cannula insertion mechanism may further include a cannula insertion spring configured to move the cannula from a first pre-insertion position to a second post-insertion position.

The cannula insertion mechanism further includes a trigger arm configured to hold the cannula insertion spring such that the cannula is in the first pre-insertion position and configured to release the insertion spring such that the cannula moves to the second post-insertion position.

The drive mechanism may further include a first gear member configured to rotate the first rotatable shaft member when the first expandable member is moved between the first position and the second position.

The first gear member may include a first portion configured hold the trigger arm in a first position such that the cannula is in the first pre-insertion position and a second portion configured to release the trigger arm to a second position such that the cannula is allowed to move to the second post-insertion position.

The drive mechanism may rotate the first gear member from the first portion to the second portion by moving the first expandable member between the first position and the second position to thereby release the trigger arm and insert the cannula into the user.

The cannula insertion mechanism may be further configured to insert a sensor into the user.

The sensor may include a continuous glucose sensor.

The treatment system may further include a controller configured to activate the drive mechanism to deliver an amount of the first fluid based on data received from the sensor.

Features and/or utilities of the present general inventive concept may also be achieved by providing a treatment system configured to treat a condition using a first therapeutic agent and a second therapeutic agent, the treatment system including a first reservoir configured to store a first fluid, a second reservoir configured to store a second fluid, a cannula insertion mechanism configured to insert a cannula into a user, the cannula in fluid communication with the first and second reservoirs, a first rotatable shaft member configured to pull a first plunger disposed within the first reservoir and coupled to by a first flexible member, a second rotatable shaft member configured to pull a second plunger disposed within the second reservoir and coupled to by a second flexible member, and a drive mechanism having a first expandable member and a second expandable member, each configured to move from a first position to a second position to rotate one shaft member to deliver a fluid.

The first fluid may include a first therapeutic agent.

The second fluid may include a second therapeutic agent.

The cannula insertion mechanism may further include a cannula insertion spring configured to move the cannula from a first pre-insertion position to a second post-insertion position.

The cannula insertion mechanism may further include a trigger arm configured to hold the cannula insertion spring such that the cannula is in the first pre-insertion position and configured to release the insertion spring such that the cannula moves to the second post-insertion position.

The drive mechanism may further include a first gear member configured to rotate the first rotatable shaft member when the first expandable member is moved between the first position and the second position.

The first gear member may include a first portion configured hold the trigger arm in a first position such that the cannula is in the first pre-insertion position and a second portion configured to release the trigger arm to a second position such that the cannula is allowed to move to the second post-insertion position.

The drive mechanism may rotate the first gear member from the first portion to the second portion by moving the first expandable member between the first position and the second position to thereby release the trigger arm and insert the cannula into the user.

The cannula insertion mechanism may be further configured to insert a sensor into the user.

The sensor may include a continuous glucose sensor.

The treatment system may further include a controller coupled with the circuit board an configured to activate the drive mechanism to deliver an amount of the first fluid based on data received from the sensor.

Additional aspects of the present general inventive concept will be set forth in part in the description which follows and, in part, will be obvious from the description, or may be learned by practice of the general inventive concept.

BRIEF DESCRIPTIONS OF THE DRAWINGS

These and/or other aspects of the present general inventive concept will become apparent and more readily appreciated from the following description of the embodiments, taken in conjunction with the accompanying drawings of which:

FIG. 5A is a bottom perspective view of the treatment system illustrated in FIG. 4;

FIG. 5B is an enlarged detail view of item 'B' illustrated in FIG. 5A;

DETAILED DESCRIPTION

Figure 1:
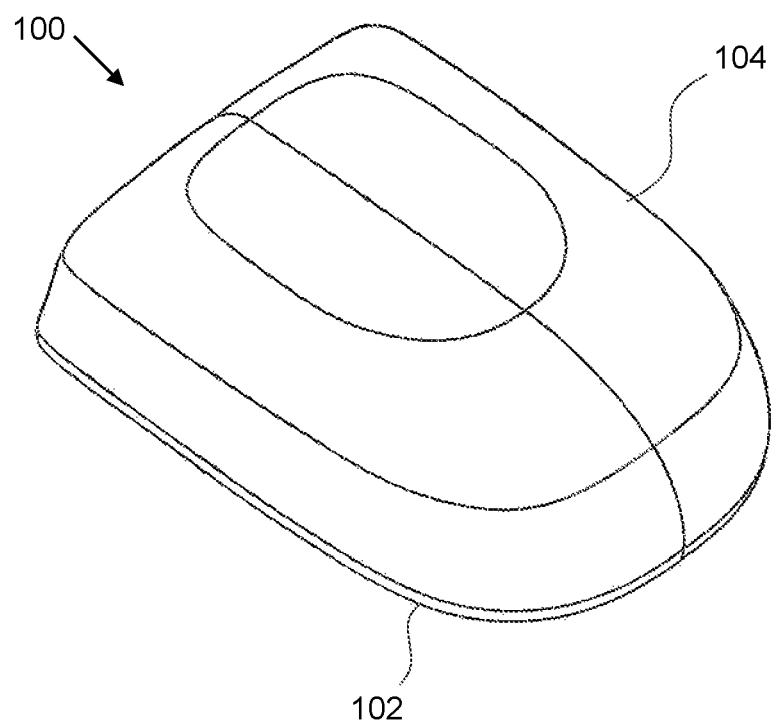
FIG. 1 is a top perspective view of a treatment system according to an exemplary embodiment of the present general inventive concept.

Reference will now be made in detail to the exemplary embodiments of the present general inventive concept, examples of which are illustrated in the accompanying drawings, wherein like reference numerals refer to the like elements throughout. The exemplary embodiments are described below in order to explain the present general inventive concept by referring to the figures.

Figure 2:
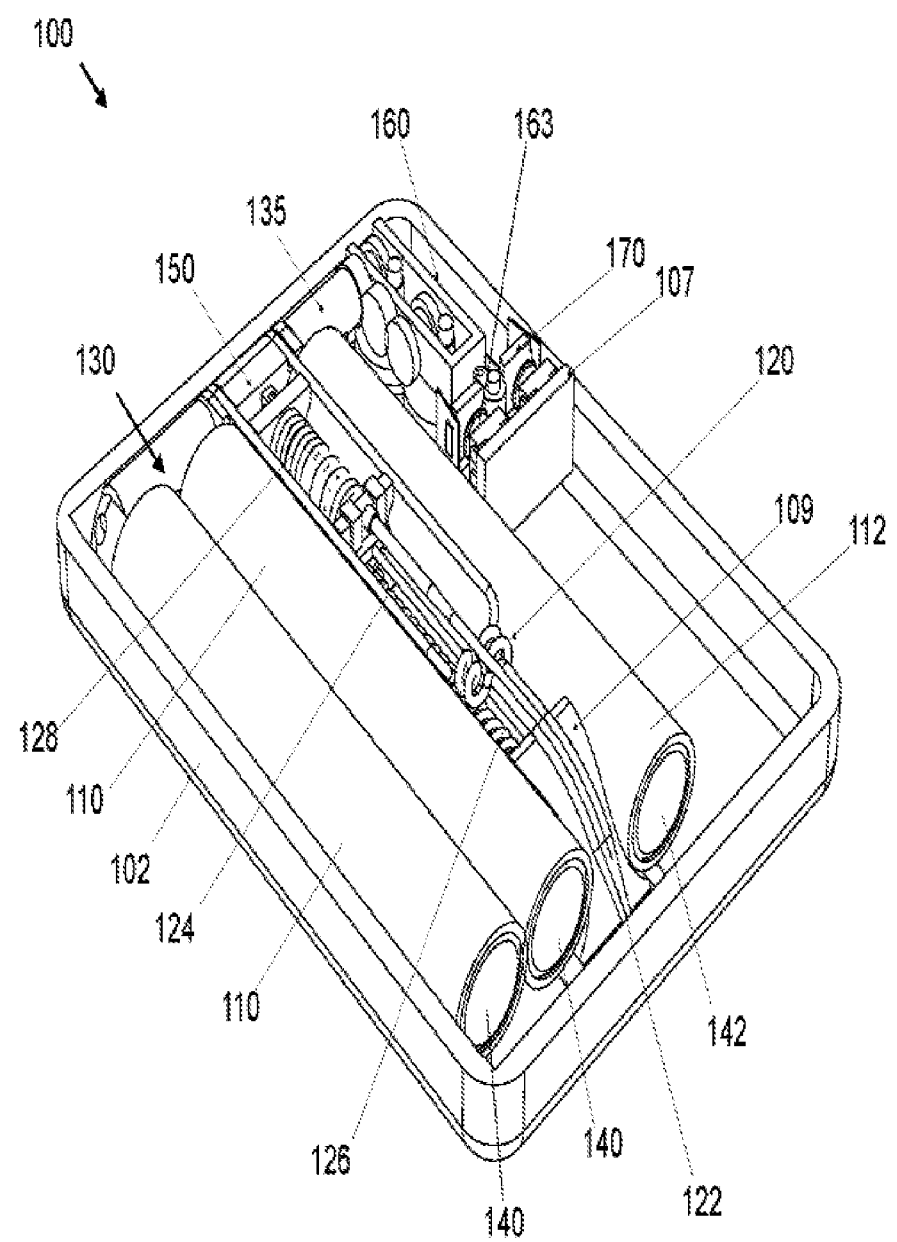
FIG. 2 is a top perspective view of the treatment system illustrated in FIG. 1, with a top housing removed.

FIG. 1 is a top perspective view of a treatment system 100 according to an exemplary embodiment of the present general inventive concept. FIG. 2 is a top perspective view of the treatment system 100 illustrated in FIG. 1, with a top housing 104 removed.

Referring to FIGS. 1 and 2, according to an exemplary embodiment of the present general inventive concept, the treatment system 100 is configured to treat a user 10 having various conditions or diseases, such as diabetes and/or various other chronic diseases.

In alternative exemplary embodiments, the treatment system 100 may be configured to treat a variety of diseases and/or conditions in humans and/or animals, wherein a first fluid 110a may include a first therapeutic agent used for the treatment of such diseases or conditions. However, the present general inventive concept is not limited thereto.

In the present exemplary embodiment, the treatment system 100 includes a base housing 102 and a top housing 104 configured to enclose and seal exemplary embodiments of a first reservoir 110 configured to receive and store a first fluid 110a (e.g., a first therapeutic agent), a cannula and sensor insertion mechanism 120 configured to insert a cannula 122 and a sensor 124 into a user 10 thereby providing fluid communication between the first reservoir 110 and the user 10 through the cannula 122 and the ability to monitor particular body signals of the user 10 using the sensor 124, a first rotatable shaft member 130 configured to wind-up or pull a first plunger 140 disposed within the first reservoir 110 and coupled to the first rotatable shaft member 130 by a first flexible member 132 (see FIG. 11), a manifold 150 configured to provide fluid communication between the one or more reservoirs 110 and the cannula 122, and a drive mechanism 160 having one or more expandable members 162, 165 configured to move from a first position to a second position to rotate the first rotatable shaft member 130 and deliver the first fluid 110a stored within the first reservoir 110 to the user 10 through the cannula 122. However, the present general inventive concept is not limited thereto.

In exemplary embodiments, the treatment system 100 may further include a top housing 104 which is configured to be coupled and sealed to the base housing 102 such that an interior of the treatment system 100 is waterproof and/or water resistant from an exterior environment.

In exemplary embodiments, the treatment system 100 may further include an additional first reservoir 110 also having a first plunger 140 to accommodate a desired volume of the first fluid 110a which is to be delivered to the user 10.

In exemplary embodiments, the flexible member 132 may be constructed from a stainless-steel material or various other non-toxic and human safe materials and compatible with various fluids which are stored within the fluid reservoirs 110 and administered to the user 10.

In the present exemplary embodiment, the treatment system 100 includes a circuit board 106 to control operations of the treatment system 100, a heat source 107 to expand one or more actuators 163, 164, 166, 167, and a re-chargeable power supply 108 to provide power to the circuit board 106 and the heat source 107. The circuit board 106 may further communicate with a sensor 124 to control an amount of fluid administered from the one or more fluid reservoirs 110 by controlling the activation of the one or more actuators 163, 164, 166, 167.

In alternative exemplary embodiments, the treatment system 100 is configured to be partially re-usable, wherein the power supply 108, the circuit board 106 and/or the heat source 107 may be detachably coupled to the base housing 102. However, the present general inventive concept is not limited thereto.

In alternative exemplary embodiments, the treatment system 100 may be configured to include a first reservoir 110 used to store a first fluid (e.g., insulin) and a second fluid reservoir 112 used to store a second fluid (e.g., glucagon). In an exemplary embodiment, the treatment system 100 may be configured to receive data from the sensor 124 regarding the user's glucose level and then calculate or otherwise determine an amount of the first fluid 110a (e.g., insulin) that is to be delivered from the first reservoir 110 and/or an amount of the second fluid 112a (e.g., glucagon) that is to be delivered from the second reservoir 112 based on the user's glucose level. However, the present general inventive concept is not limited thereto.

That is, in alternative embodiments, the treatment system 100 may be configured to receive data from other various sensors, including a heart rate sensor to determine an amount of the first and/or second fluid to deliver to the user 10.

Figure 3A:
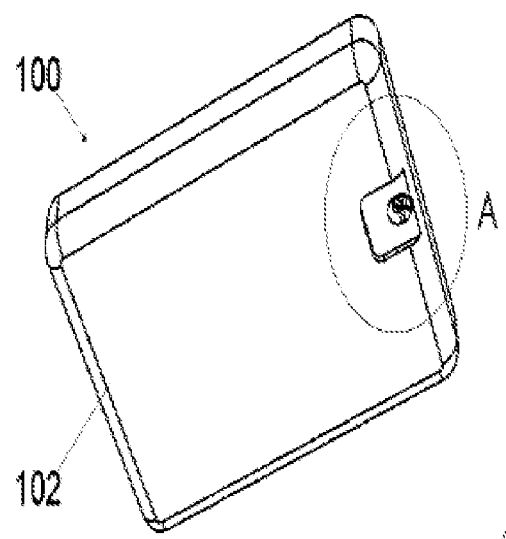
FIG. 3A is a bottom perspective view of the treatment system illustrated in FIG. 1.
Figure 3B:
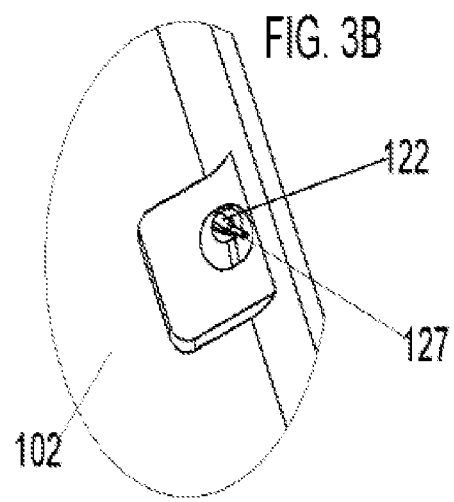
FIG. 3B is an enlarged detail view of item 'A' illustrated in FIG. 3A.
Figure 4:
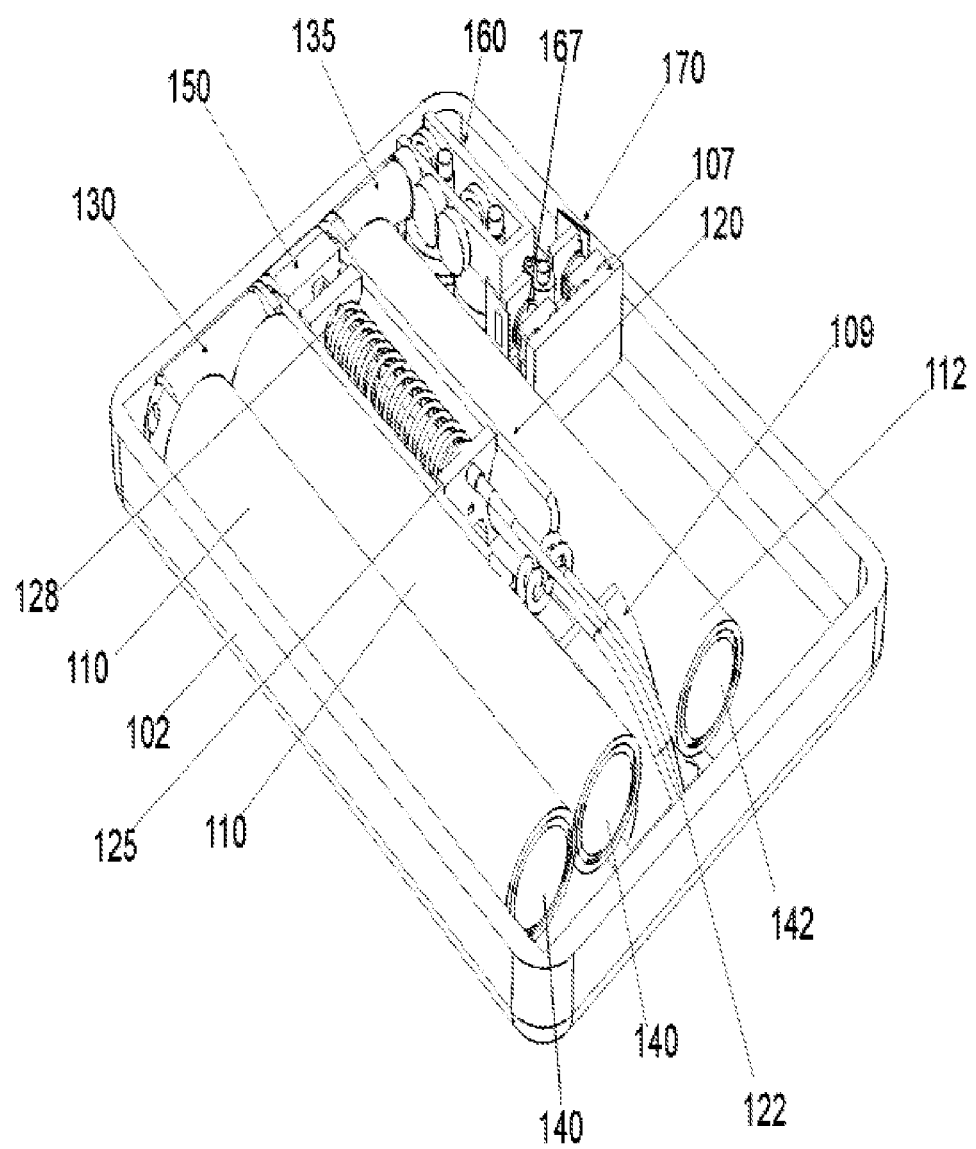
FIG. 4 is a top perspective view of the treatment system illustrated in FIG. 1, wherein the cannula and sensor insertion mechanism is in a mid-deployed state according to an example embodiment of the present general inventive concept.
Figure 6:
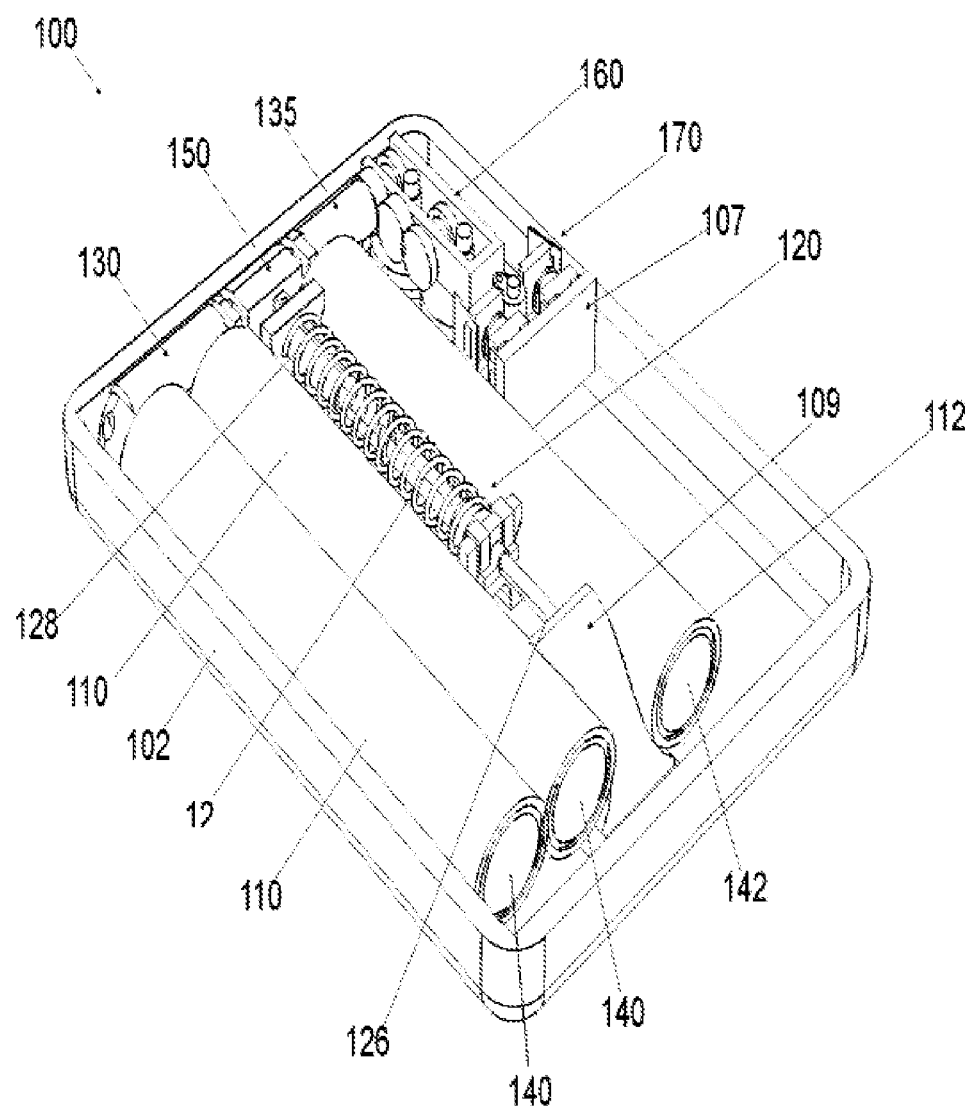
FIG. 6 is a top perspective view of the treatment system illustrated in FIG. 1, wherein the cannula and sensor inserter are in a post-deployed state according to an example embodiment of the present general inventive concept.
Figure 7A:
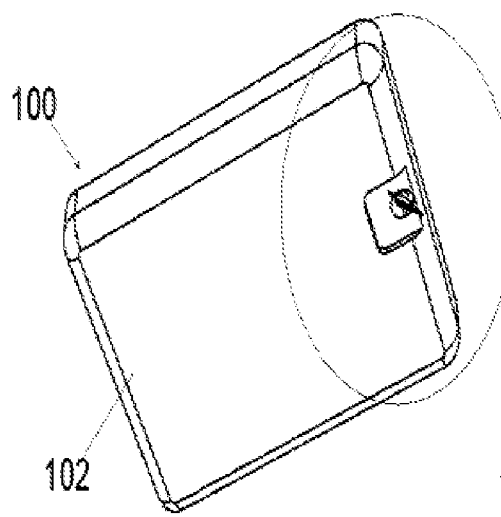
FIG. 7A is a bottom perspective view of the treatment system illustrated in FIG. 6.
Figure 7B:
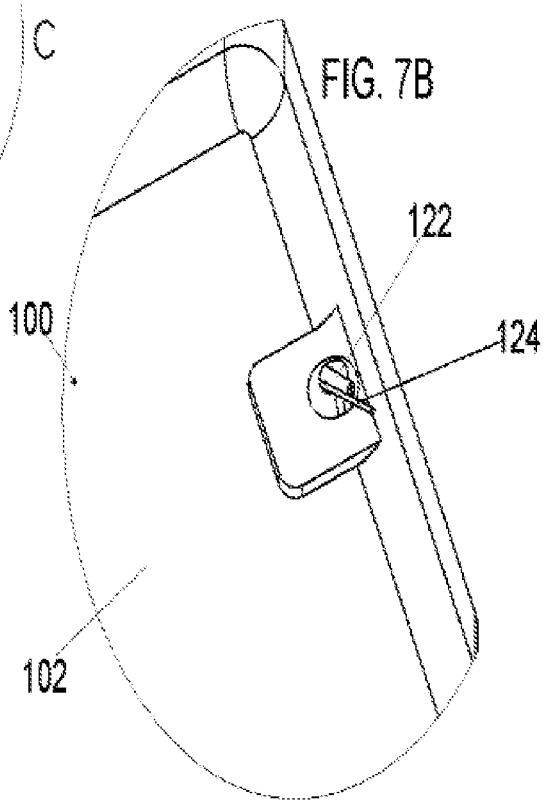
FIG. 7B is an enlarged detail view of item 'C' illustrated in FIG. 7A.
Figure 8:
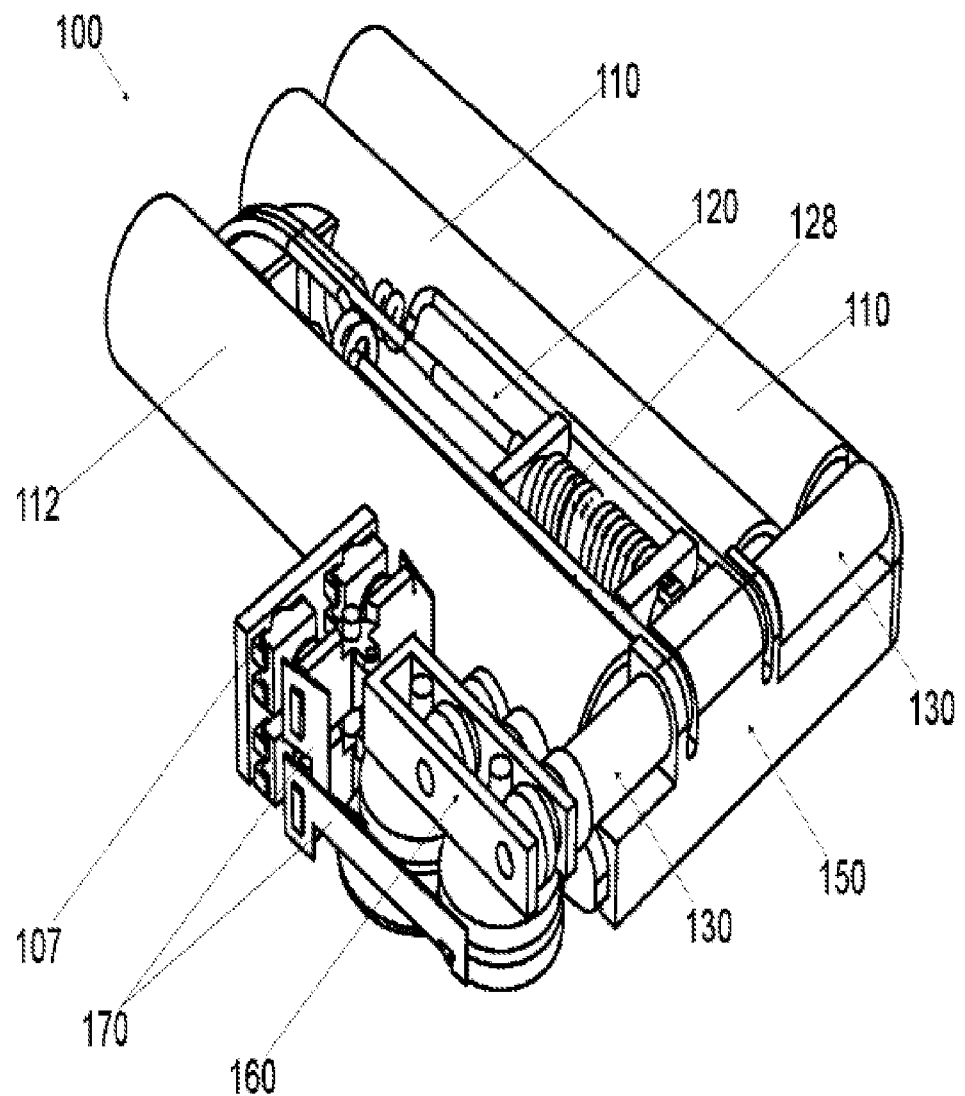
FIG. 8 is a back-perspective view of the treatment system illustrated in FIG. 1, with a top and base housing removed.
Figure 9:
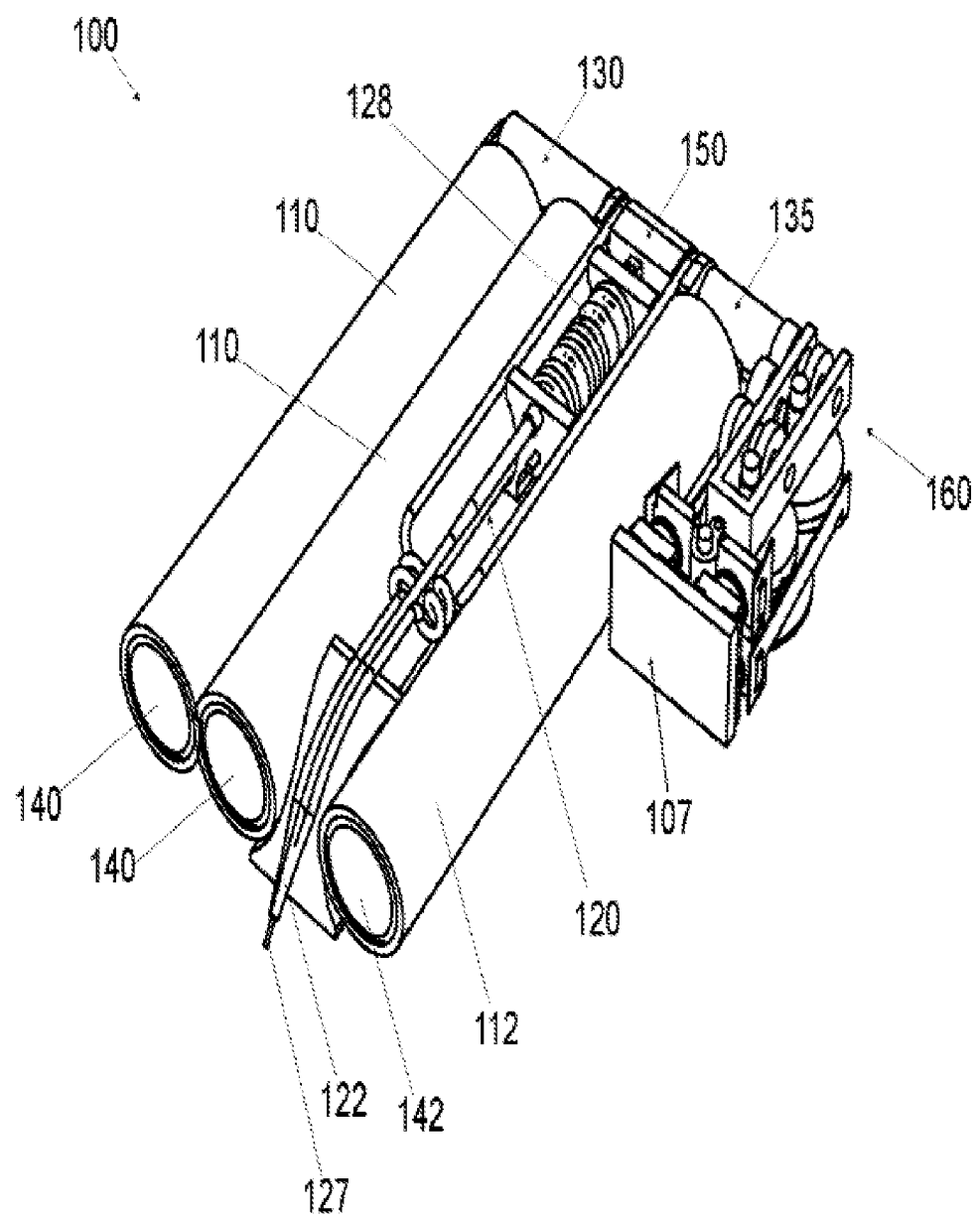
FIG. 9 is a front perspective view of the treatment system illustrated in FIG. 8.

FIG. 3A is a bottom perspective view of the treatment system illustrated in FIG. 1 and FIG. 3B is an enlarged detail view of item 'A' illustrated in FIG. 3A. FIG. 4 is a top perspective view of the treatment system illustrated in FIG. 1, wherein the cannula and sensor insertion mechanism is in a mid-deployed state according to an example embodiment of the present general inventive concept. FIG. 5A is a bottom perspective view of the treatment system illustrated in FIG. 4 and FIG. 5B is an enlarged detail view of item 'B' illustrated in FIG. 5A. FIG. 6 is a top perspective view of the treatment system illustrated in FIG. 1, wherein the cannula and sensor inserter are in a post-deployed state according to an example embodiment of the present general inventive concept. FIG. 7A is a bottom perspective view of the treatment system illustrated in FIG. 6 and FIG. 7B is an enlarged detail view of item 'C' illustrated in FIG. 7A.

The cannula and sensor insertion mechanism 120 is configured to insert a cannula 122 and a sensor 124 into a user 10. However, in alternative embodiments, the cannula and sensor insertion mechanism 120 may be configured to insert one or more cannulas 122 and/or one or more sensors 124 into the user 10.

In the present exemplary embodiment, the cannula insertion mechanism 120 may further include a cannula insertion spring 126 which is configured to move the cannula 122 (e.g., a soft flexible cannula) from a first pre-insertion position 122a (see FIG. 3B) to a second post-insertion position 122b (see FIG. 7B), an introducer needle 127 which is disposed in at least a portion of the cannula 122 and is configured to insert the cannula 122 into the user 10, a needle retraction spring 128 which is configured to remove or partially retract the introducer needle 127 from within the cannula 122, after the cannula 122 is inserted into the user 10 (see FIG. 7B), and a trigger arm 129 configured to hold the cannula insertion spring 126 such that the cannula 122 is in the first pre-insertion position 122a and configured to release the insertion spring 126 such that the cannula 122 moves to the second post-insertion position 122b.

That is, in the present embodiment, the cannula insertion spring 126 may be used to push the introducer needle 127 and cannula 122 toward and into the user 10 such that the introducer needle 127 initially penetrates the skin to allow the cannula 122 to be inserted into the user 10, and then the needle retraction spring 128 may be used to retract the introducer needle 127 from within the cannula 122, thereby allowing the cannula 122 to remain inserted into the user 10 while maintaining fluid communication with at least one reservoir 110. However, the present general inventive concept is not limited thereto.

Referring to FIG. 3B, the introducer needle 127 is disposed within the cannula 122 and remains flush a bottom surface of the base housing 102. Once the trigger arm 129 is released, the cannula 122, the introducer needle 127, and the sensor 124 move toward and into the user 10 (see FIG. 5B), wherein the cannula 122, the introducer needle 127, and the sensor 124 extend beyond the bottom surface of the base housing 102. Once the retract trigger 180 contacts a surface 109a of a insertion guide member 109, a needle retraction spring 128 is allowed to release in order to retract the introducer needle 127, thereby allowing the cannula 122 and the sensor 124 to remain inserted inside of the user 10 (see FIG. 7B).

In alternative embodiments, the cannula 122 may include a tri-lumen structure wherein a first lumen 122a may be in fluid communication with a first reservoir 110, a second lumen 122b may be in fluid communication with a second reservoir 112, and a third lumen 122c may be used to house the introducer needle 127. As such, there exists a first fluid path between the cannula 122 and the first reservoir 110 through the first lumen 122a to administer the first fluid or therapeutic agent and a second fluid path between the cannula 122 and the second reservoir 112 through the second lumen 122b to administer the second fluid or therapeutic agent. However, the present general inventive concept is not limited thereto.

In alternative exemplary embodiments, the cannula insertion spring 126 may also be used to push a sensor 124 toward and into the user 10 such that the introducer needle 127 initially penetrates the skin to allow the cannula 122 and/or the sensor 124 to be inserted into the user 10, and then the needle retraction spring 128 may be used to retract the introducer needle 127 from within the cannula 122, thereby allowing the cannula 122 and the sensor 124 to remain inserted into the user 10 while maintaining fluid communication with at least one reservoir 110. However, the present general inventive concept is not limited thereto.

In exemplary embodiments, the sensor 124 may be configured for integrated continuous monitoring of the user's 10 glucose levels, such as a continuous glucose monitor (CGM). The sensor 124 may be configured to be integrated with wireless or wired communication such that once inserted, the sensor 124 may continuously transmit data or information of the user's glucose levels to the circuit board 106.

In the present exemplary embodiment, during a single uninterrupted action, when the trigger arm 129 is released, the cannula insertion spring 126 pulls the slide insert 125 which is coupled to the introducer needle 127 and cannula 122 toward an insertion guide member 109. Once the retract trigger 180 protruding from the slide insert 125 contacts a surface 109a of the guide member 109, the needle retraction spring 128 is allowed to release, thereby retracting the introducer needle 127 and allowing the cannula 122 and sensor 124 to remain inserted in the user 10.

In exemplary embodiments, the cannula insertion mechanism 120 is configured to automatically insert a cannula 122 into a user at a predetermined angle and depth and retract the introducer needle 127 based on a profile of the guide member 109. However, the present general inventive concept is not limited thereto. In exemplary embodiments, the cannula 122 may be inserted at an angle between 2 degrees and 95 degrees to a depth of 0.5 mm to 15 mm. However, the insertion angle and depth of the cannula 122 may vary as needed.

In exemplary embodiments, the treatment system 100 is used to subcutaneously and/or transcutaneously deliver a therapeutic agent (i.e., a first fluid) such as medicine, hormones, steroids, or various other fluids to a user. However, the present general inventive concept is not limited thereto. That is, in alternative exemplary embodiments, the treatment system 100 may also be used to deliver nano-particles, nano-medicines, insulin, glucagon, antibiotics, morphine, gene therapy medicines, AZT, chemotherapy medications, or the like. In addition, in alternative exemplary embodiments, the treatment system 100 may include one or more reservoirs 110 configured to deliver one or more fluids required for treating various types of conditions and/or diseases. Although not illustrated, the present general inventive concept may be embodied with a single fluid reservoir 110 and/or multiple fluid reservoirs 110, as needed.

In the present exemplary embodiment, the drive mechanism 160 includes a first expandable member 162 having one or more actuator members 163, 164. Each actuator member 163,164 consists of a propellant sealed within an expandable membrane or foil. As heat (e.g., from the heat source 107) is applied to the actuator member 163, 164, the propellant disposed within the expandable membrane expands causing the expandable membranes of the actuator members 163, 164 to expand. As such, by disposing a first actuator 163 on a first side of a first gear member 168 and a second actuator 164 on a second side of the first gear member 168, the gear 168 may be forced to rotate by alternating the application of heat to the first actuator 163 and the second actuator 164. In addition, the first and second actuator members 163 and 164 may be coupled to a pivotally coupled gear pusher 170, such that application of heat to the first actuator 163 may push the first gear and application of heat to the second actuator 164 may pull the first gear. As a result, the gear may be rotated in the same direction (e.g., clockwise) when either of the first and second actuators 163, 164 are exposed to heat.

In exemplary embodiments, the drive mechanism 160 includes a plurality of gears which translates a linear motion of the first expandable member 162 into rotation of the first rotatable shaft member 130 to thereby wind up the first plunger 140 disposed within the first reservoir 110 and deliver the first fluid 110a to the user 10 through the cannula 122. In the present embodiment, the drive mechanism 160 includes a first gear member 168 configured to rotate the first rotatable shaft member 130 when the actuators 163, 164 of the first expandable member 162 is moved between the first position and the second position.

In exemplary embodiments, the first gear member 168 includes a first portion 168a configured hold the trigger arm 129 in a first position 129a such that the cannula 122 is in the first pre-insertion position 122a and a second portion 168b configured to release the trigger arm 129 to a second position 129b such that the cannula 122 is allowed to move to the second post-insertion position 122b. The drive mechanism 160 rotates the first gear member 168 from the first portion 168a to the second portion 168b by moving the actuators 163, 164 of the first expandable member 162 between the first position and the second position to thereby release the trigger arm 129 and insert the cannula 122 into the user 10.

In the present exemplary embodiment, the treatment system 100 includes a single fluid reservoir 110, a cannula insertion mechanism 120, a first rotatable shaft member 130, a manifold 150, a drive mechanism 160, and a first expandable member 160a including first and second actuator members 162, 163. A user 10 may insert a syringe into a fill port 152 of the manifold 150 in order to fill the fluid reservoir 110 with a first fluid 110a or therapeutic agent. As the fluid enters the fill port 152, the fluid passes into the reservoir 110 through the manifold 150 thereby pushing the plunger 140 disposed within the fluid reservoir 110 away from the manifold 150. The first rotatable shaft member 130 is allowed to rotate to allow the flexible member 132 coupled to the plunger 140 to unwind and allow the plunger 140 to move away from the manifold 150.

The actuators 163, 164 of the first expandable members 162 are heated in alternating fashion in order to rotate the first rotatable shaft member 130 which, in turn, winds up the first flexible member 132 around the shaft member 130 and forces the first fluid 110a stored within the fluid reservoir 110 through the manifold 150 into the first lumen 122a of the cannula 122 and into the user 10. However, the present general inventive concept is not limited thereto.

In alternative exemplary embodiments, the drive mechanism 160 includes a second expandable member 165 having one or more actuator members 166, 167. Each actuator member 166, 167 consists of a propellant sealed within an expandable membrane or foil. As heat (e.g., from the heat source 107) is applied to the actuator member 166, 167, the propellant disposed within the expandable membrane expands causing the expandable membranes of the actuator members 166, 167 to expand. As such, by disposing a third actuator 166 on a first side of a second gear member 169 and a fourth actuator 167 on a second side of the second gear member 169, the gear 169 may be forced to rotate by alternating the application of heat to the third actuator 166 and the fourth actuator 167. In addition, the third and fourth actuator members 166 and 167 may be coupled to a pivotally coupled gear pusher 170, such that application of heat to the third actuator 166 may push the second gear and application of heat to the second actuator 167 may pull the second gear. As a result, the second gear 169 may be rotated in the same direction (e.g., counter-clockwise) when either of the third and fourth actuators 166, 167 are exposed to heat.

In exemplary embodiments, the drive mechanism 160 includes a plurality of gears which translates a linear motion of the second expandable member 165 into rotation of the second rotatable shaft member 135 to thereby wind up the second plunger 142 disposed within the second reservoir 112 and deliver the second fluid 112a to the user 10 through the cannula 122. In the present embodiment, the drive mechanism 160 includes a second gear member 169 configured to rotate the second rotatable shaft member 135 when the actuators 166, 167 of the second expandable member 165 is moved between the first position and the second position.

In the present exemplary embodiment, the treatment system 100 includes a first fluid reservoir 110, a second fluid reservoir 112, a cannula insertion mechanism 120, a first rotatable shaft member 130, a second rotatable shaft member 135, a manifold 150, a drive mechanism 160, a first expandable member 162 including first and second actuator members 163, 164, and a second expandable member 165 including third and fourth actuator members 166, 167.

A user 10 may insert a syringe into a fill port 152 of the manifold 150 in order to fill the first fluid reservoir 110 with a first fluid 110a or therapeutic agent and into a fill port (not illustrated) in order to fill the second fluid reservoir 112 with a second fluid 112a or therapeutic agent. As the fluids enters the fill ports, the fluids respectively pass into the reservoir 110 or the reservoir 112 through the manifold 150 thereby pushing the plunger 140 disposed within the first fluid reservoir 110 and the plunger 142 disposed within the second fluid reservoir 112 away from the manifold 150. The first rotatable shaft member 130 is allowed to rotate to allow the flexible member 132 coupled to the plunger 140 to unwind and allow the plunger 140 to move away from the manifold 150. Similarly, the second rotatable shaft member 135 is allowed to rotate to allow the flexible member 136 coupled to the plunger 142 to unwind and allow the plunger 142 to move away from the manifold 150.

The actuators 163, 164 of the first expandable members 162 are heated in alternating fashion in order to rotate the first rotatable shaft member 130 which, in turn, winds up the first flexible member 132 around the shaft member 130 and forces the first fluid 110a stored within the fluid reservoir 110 through the manifold 150 into the first lumen 122a of the cannula 122 and into the user 10.

Similarly, the actuators 166, 167 of the second expandable members 165 are heated in alternating fashion in order to rotate the second rotatable shaft member 135 which, in turn, winds up the second flexible member 136 around the shaft member 135 and forces the first fluid 112a stored within the fluid reservoir 112 through the manifold 150 into the second lumen 122b of the cannula 122 and into the user 10.

Figure 10:
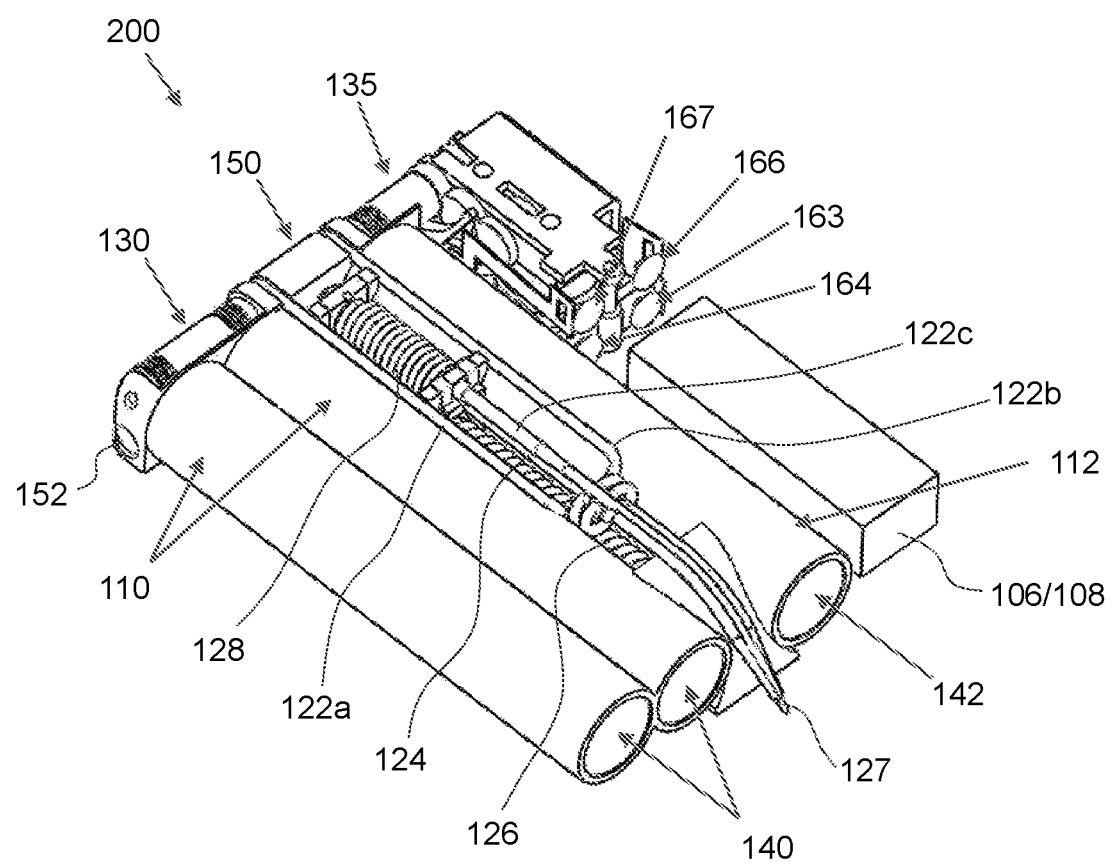
FIG. 10 is a top perspective view of a treatment system according to another exemplary embodiment, with a top housing and a base housing removed.
Figure 11:
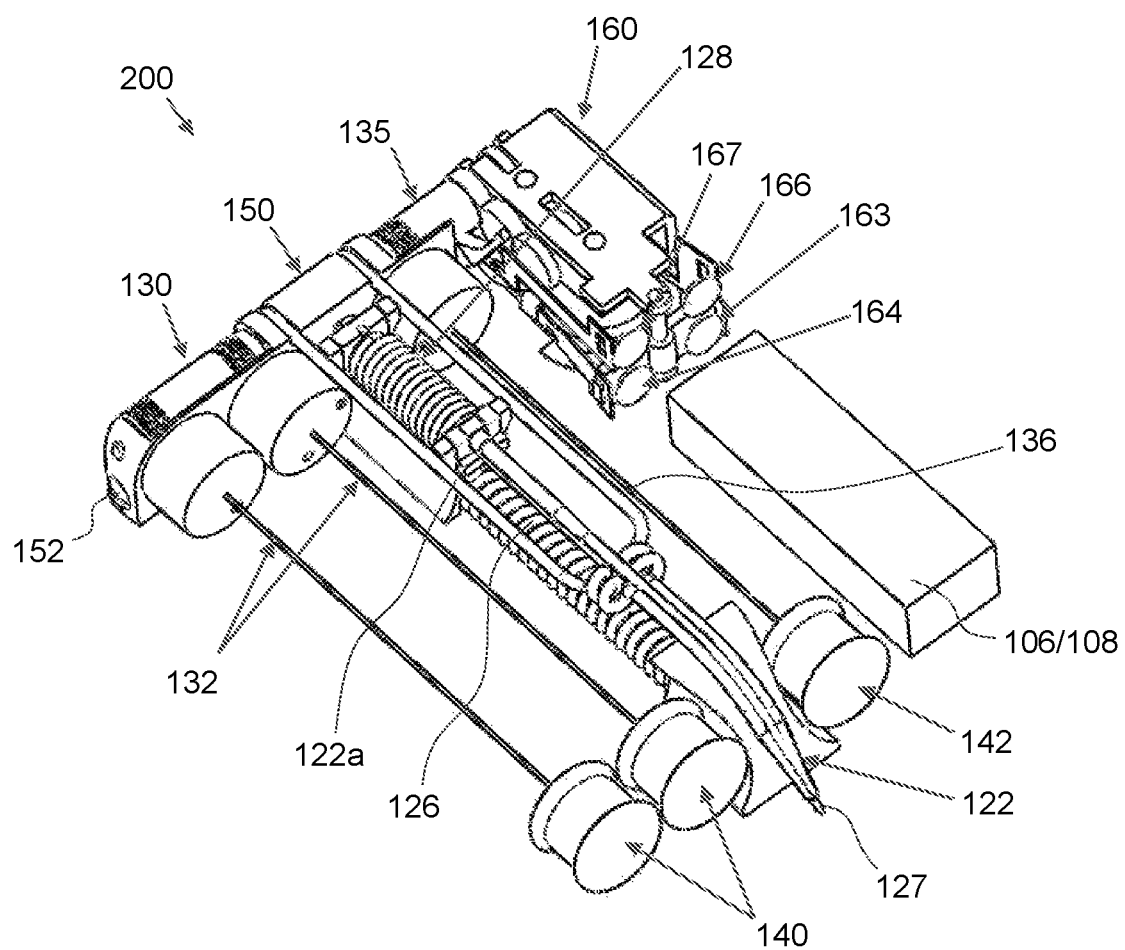
FIG. 11 is a top perspective view of the treatment system illustrated in FIG. 10, with the fluid reservoirs removed.
Figure 12:
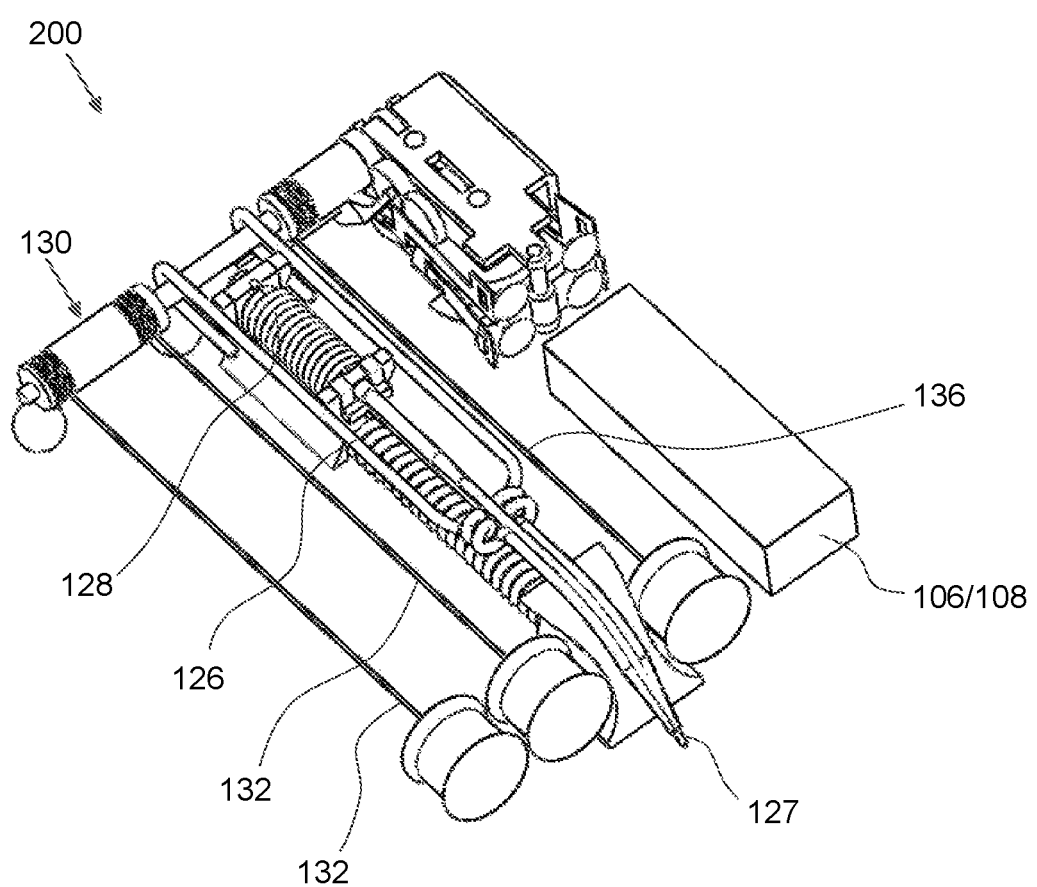
FIG. 12 is a top perspective view of the treatment system illustrated in FIG. 11, with the manifold removed.
Figure 13:
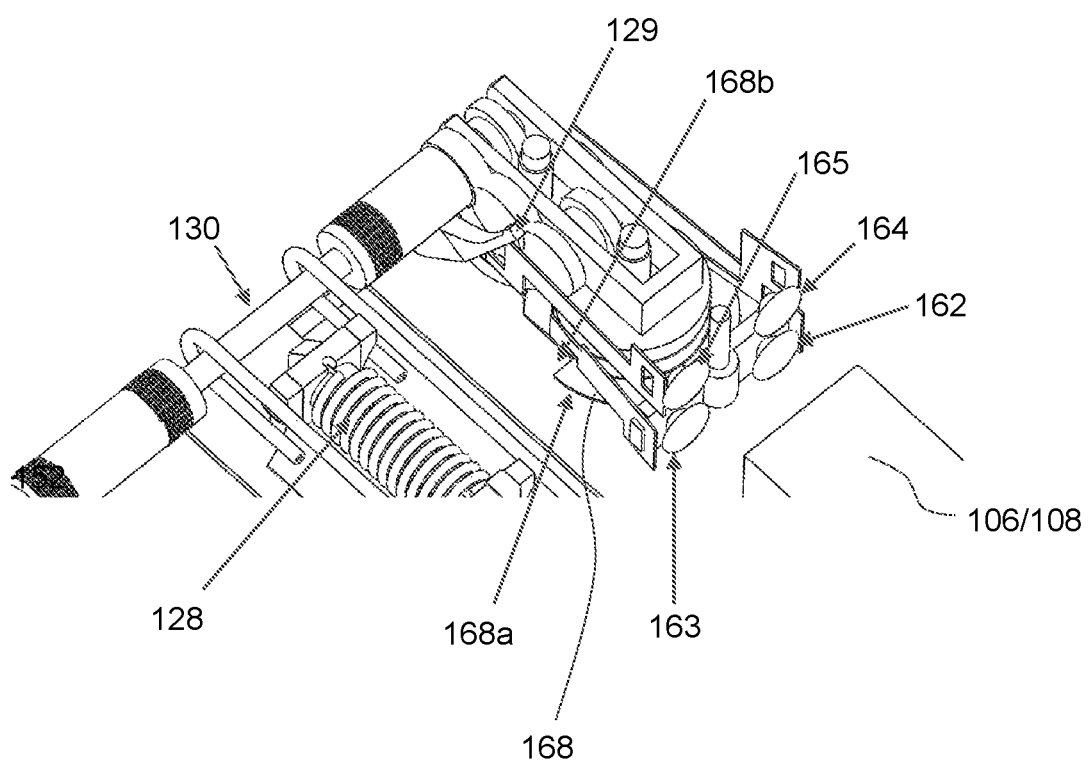
FIG. 13 is a top perspective view of the treatment system illustrated in FIG. 12, with a drive mechanism cover removed.
Figure 14:
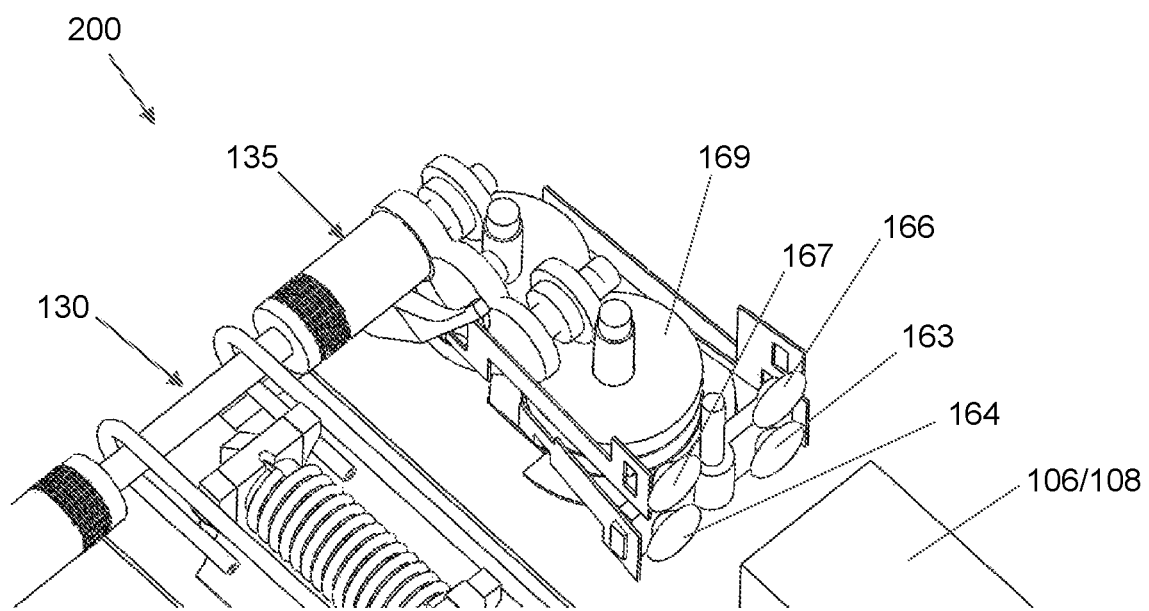
FIG. 14 is a top perspective view of the treatment system illustrated in FIG. 13, with a drive mechanism guide member removed.
Figure 15:
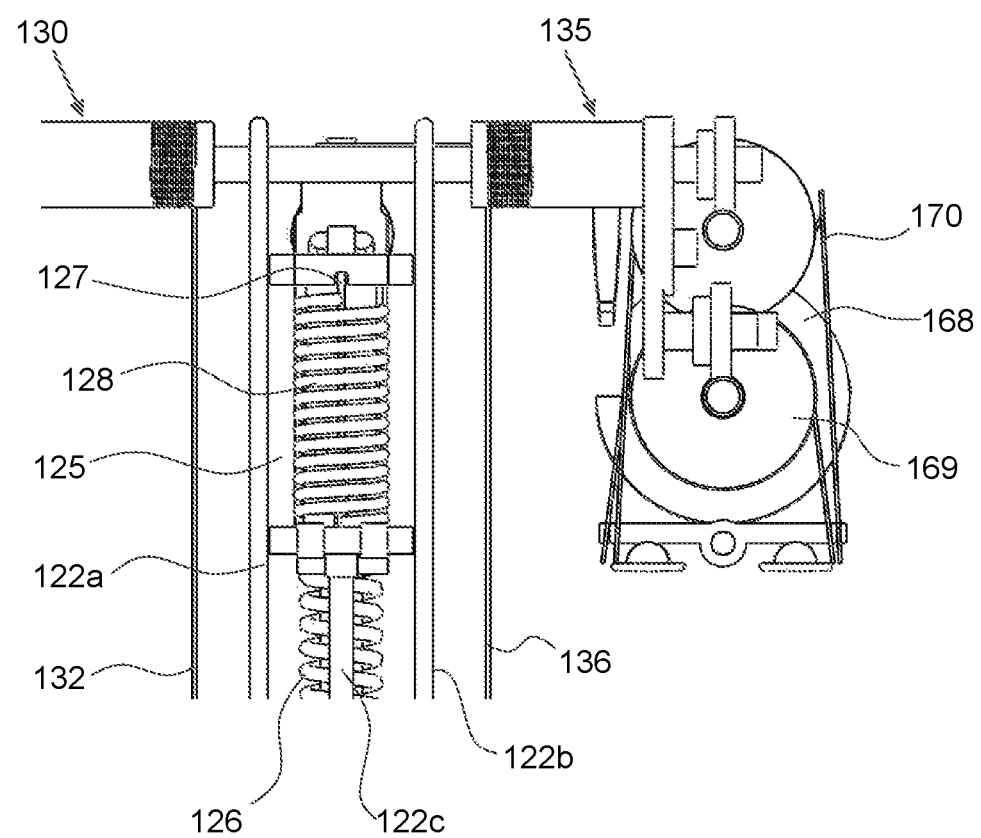
FIG. 15 is a top view of the drive mechanism of the treatment system illustrated in FIG. 14.
Figure 16:
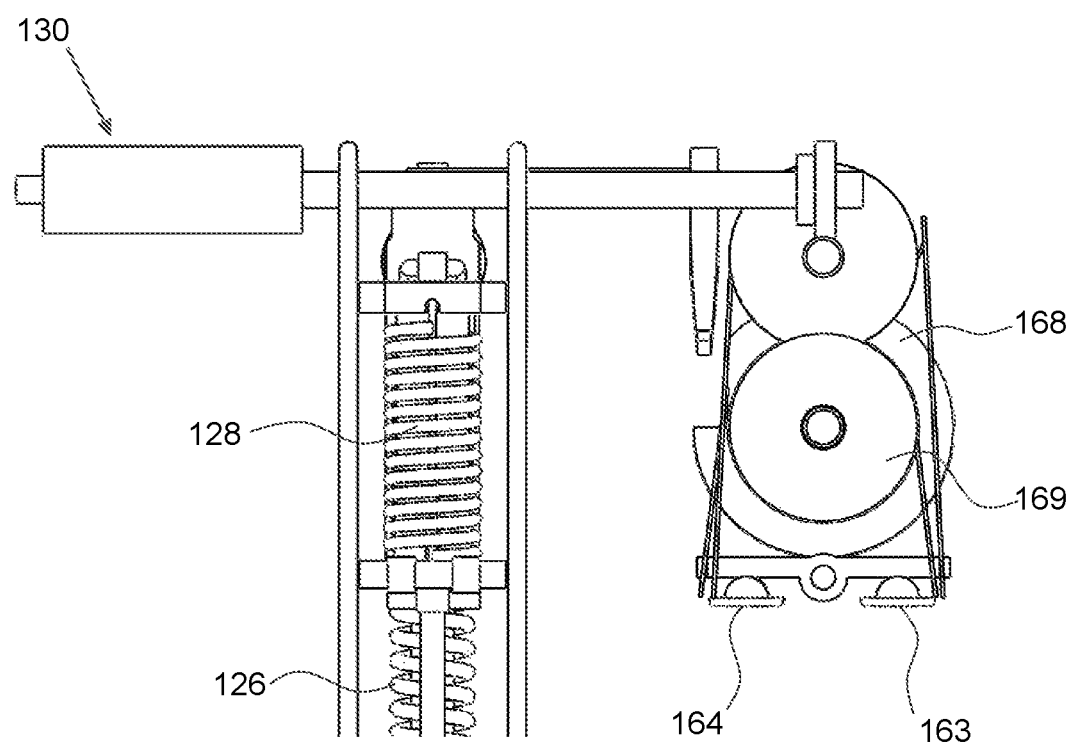
FIG. 16 is a top view of the drive mechanism of the treatment system illustrated in FIG. 15, with a second rotatable shaft member removed.
Figure 17:
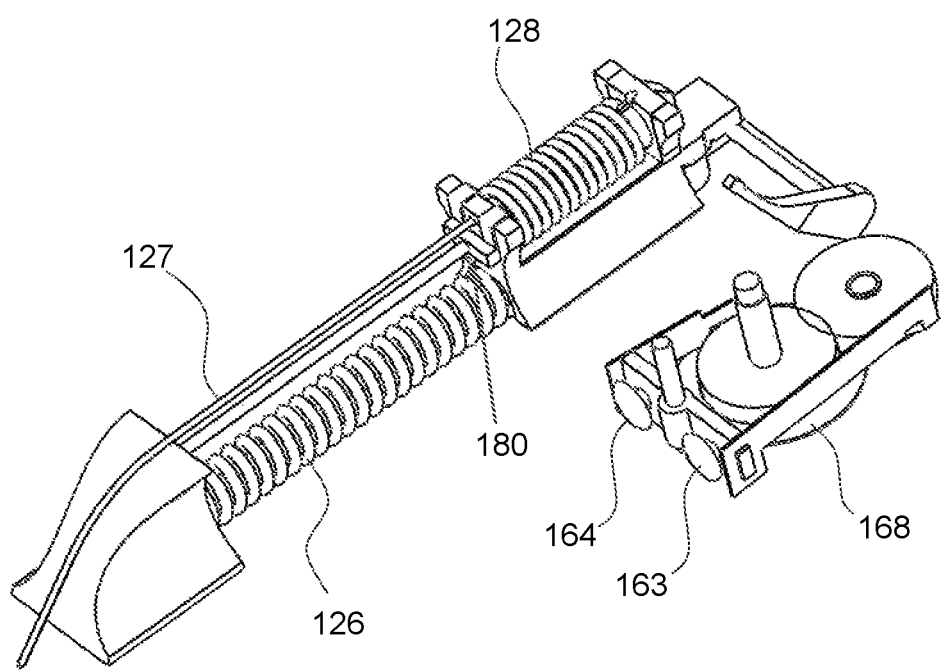
FIG. 17 is a front perspective view of the cannula and sensor inserter of the treatment system illustrated in FIG. 10.
Figure 18:
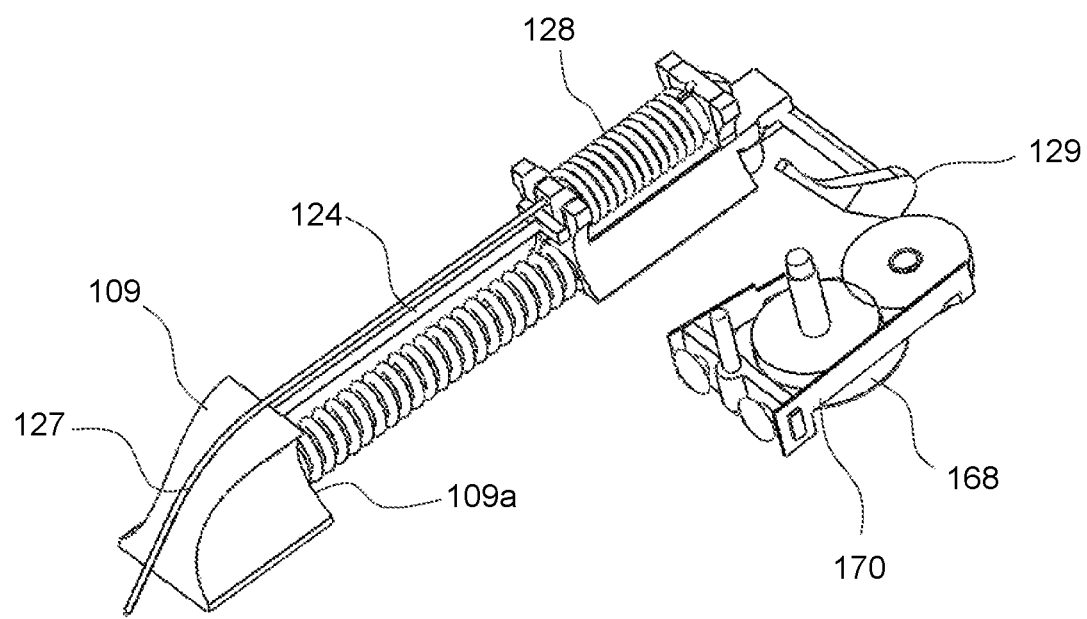
FIG. 18 is a side perspective view of the cannula and sensor inserter of the treatment system illustrated in FIG. 17.
Figure 19:
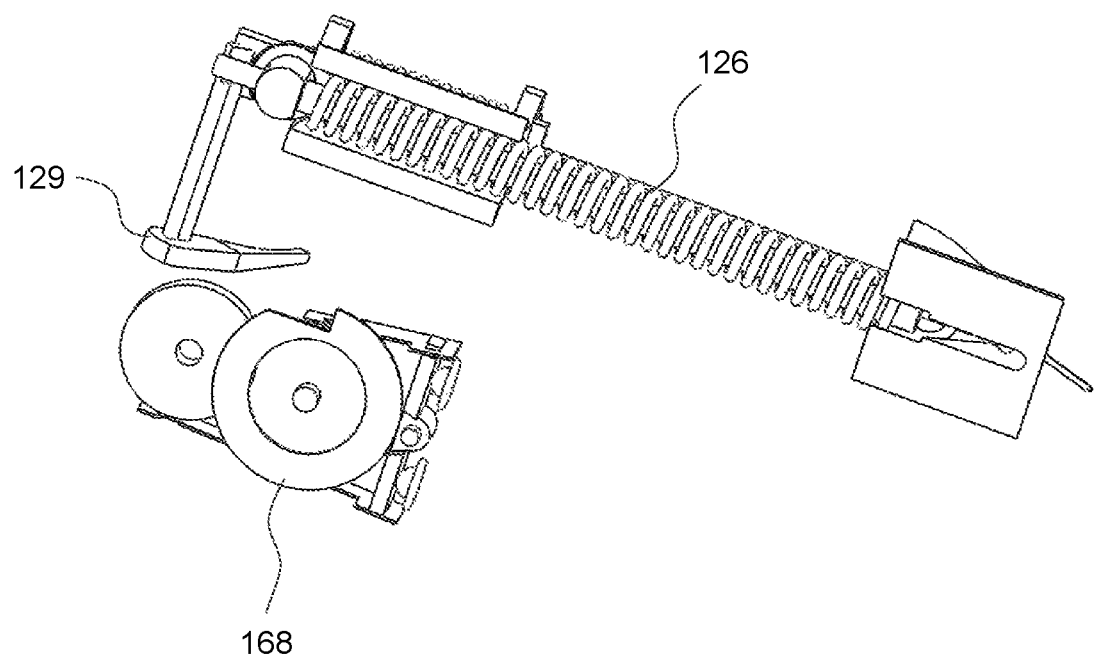
FIG. 19 is a bottom perspective view of the cannula and sensor inserter of the treatment system illustrated in FIG. 17.

FIG. 10 is a top perspective view of a treatment system 200 according to another exemplary embodiment, with the top housing and base housing removed. FIG. 11 is a top perspective view of the treatment system illustrated in FIG. 10, with the fluid reservoirs removed. FIG. 12 is a top perspective view of the treatment system illustrated in FIG. 11, with the manifold removed. FIG. 13 is a top perspective view of the treatment system illustrated in FIG. 12, with a drive mechanism cover removed. FIG. 14 is a top perspective view of the treatment system illustrated in FIG. 13, with a drive mechanism guide member removed.

That is, in alternative exemplary embodiments, the treatment system 200 is configured to treat a condition using a first therapeutic agent and a second therapeutic agent, the treatment system 200 includes a first reservoir 110 configured to store a first fluid, a second reservoir 112 configured to store a second fluid, a cannula insertion mechanism 120 configured to insert a cannula 122 into a user 10, the cannula 122 in fluid communication with the first and second reservoirs 110, 112, a first rotatable shaft member 130 configured to pull a first plunger 140 disposed within the first reservoir 110 and coupled to by a first flexible member 132, a second rotatable shaft member 135 configured to pull a second plunger 142 disposed within the second reservoir 112 and coupled to by a second flexible member 136, and a drive mechanism 160 having a first expandable member 162 and a second expandable member 165, each configured to move from a first position to a second position to rotate one shaft member to deliver a fluid.

In exemplary embodiments, the first fluid includes a first therapeutic agent and the second fluid includes a second therapeutic agent.

In exemplary embodiments, the cannula insertion mechanism further includes a cannula insertion spring configured to move the cannula from a first pre-insertion position to a second post-insertion position.

The cannula insertion mechanism further includes a trigger arm configured to hold the cannula insertion spring such that the cannula is in the first pre-insertion position and configured to release the insertion spring such that the cannula moves to the second post-insertion position.

The drive mechanism further includes a first gear member configured to rotate the first rotatable shaft member when the first expandable member is moved between the first position and the second position and a second gear member configured to rotate the second rotatable shaft member when the second expandable member is moved between a first position and a second position.

The first gear member may include a first portion configured hold the trigger arm in a first position such that the cannula is in the first pre-insertion position and a second portion configured to release the trigger arm to a second position such that the cannula is allowed to move to the second post-insertion position.

Although a few exemplary embodiments of the present general inventive concept have been illustrated and described, it will be appreciated by those skilled in the art that changes may be made in these exemplary embodiments without departing from the principles and spirit of the general inventive concept, the scope of which is defined in the appended claims and their equivalents.

What is claimed is:

1. A treatment system configured to treat a disease using a first therapeutic fluid, the treatment system comprising:
   a base housing;
   a first reservoir configured to store a first therapeutic fluid;
   a first plunger disposed within the first reservoir;
   a first rotatable shaft member configured to rotate within the base housing;
   a sensor to monitor signals of a user;
   a first flexible member having a first end coupled to the first plunger and a second end coupled to the first rotatable shaft member,
   wherein the first rotatable shaft member is configured to shorten a length of the first flexible member to deliver the first therapeutic fluid from the first reservoir.

2. The treatment system of claim 1, further comprising a cannula in fluid communication with the first reservoir.

3. The treatment system of claim 2, further comprising a drive mechanism having a first expandable member configured to move from a first position to a second position to rotate the first rotatable shaft member to deliver the first fluid through the cannula.

4. The treatment system of claim 3, further comprising a cannula insertion mechanism configured to insert the cannula into a user.

5. The treatment system of claim 4, wherein the cannula insertion mechanism further includes a cannula insertion spring configured to move the cannula from a first pre-insertion position to a second post-insertion position.

6. The treatment system of claim 5, wherein the cannula insertion mechanism further includes a trigger arm configured to hold the cannula insertion spring such that the cannula is in the first pre-insertion position and configured to release the insertion spring such that the cannula moves to the second post-insertion position.

7. The treatment system of claim 6, wherein the drive mechanism further includes a first gear member configured to rotate the first rotatable shaft member when the first expandable member is moved between the first position and the second position.

8. The treatment system of claim 7, wherein the first gear member includes a first portion configured hold the trigger arm in a first position such that the cannula is in the first pre-insertion position and a second portion configured to release the trigger arm to a second position such that the cannula is allowed to move to the second post-insertion position.

9. The treatment system of claim 8, wherein the drive mechanism rotates the first gear member from the first portion to the second portion by moving the first expandable member between the first position and the second position to thereby release the trigger arm and insert the cannula into the user.

10. The treatment system of claim 1, further comprising a controller configured to activate a drive mechanism to deliver an amount of the first therapeutic fluid to the user based on data received from the sensor.

11. A treatment system configured to treat a disease using a first therapeutic agent and a second therapeutic agent, the treatment system comprising:
- a base housing;
- a first reservoir configured to store a first therapeutic fluid and a second reservoir configured to store a second therapeutic fluid;
- a first plunger disposed within the first reservoir and a second plunger disposed within the second reservoir;
- first and second rotatable shaft members configured to rotate within the base housing;
- a first flexible member having a first end coupled to the first plunger and a second end coupled to the first rotatable shaft member;
- a second flexible member having a first end coupled to the second plunger and a second end coupled to the second rotatable shaft member,
- wherein the first rotatable shaft member is configured to shorten a length of the first flexible member to deliver the first therapeutic fluid from the first reservoir and the second rotatable shaft member is configured to shorten a length of the second flexible member to deliver the second therapeutic fluid from the second reservoir.

12. The treatment system of claim 11, further comprising a cannula in fluid communication with the first reservoir and the second reservoir.

13. The treatment system of claim 12, further comprising a drive mechanism having a first expandable member configured to move from a first position to a second position to rotate the first rotatable shaft member to deliver the first fluid through the cannula and a second expandable member configured to move from a first position to a second position to rotate the second rotatable shaft member to deliver the second fluid through the cannula.

14. The treatment system of claim 13, further comprising a cannula insertion mechanism configured to insert the cannula into a user.

15. The treatment system of claim 14, wherein the cannula insertion mechanism further includes a cannula insertion spring configured to move the cannula from a first pre-insertion position to a second post-insertion position.

16. The treatment system of claim 15, wherein the cannula insertion mechanism further includes a trigger arm configured to hold the cannula insertion spring such that the cannula is in the first pre-insertion position and configured to release the insertion spring such that the cannula moves to the second post-insertion position.

17. The treatment system of claim 16, wherein the drive mechanism further includes a first gear member configured to rotate the first rotatable shaft member when the first expandable member is moved between the first position and the second position and a second gear member configured to rotate the second rotatable shaft member when the second expandable member is moved between the first position and the second position.

18. The treatment system of claim 17, further comprising a sensor to monitor signals of the user.

19. The treatment system of claim 18, further comprising a controller configured to activate the drive mechanism to deliver an amount of the first therapeutic and an amount of the second therapeutic fluid to the user through the cannula based on data received from the sensor.

* * * * *